United States Patent
Kuo et al.

(10) Patent No.: US 8,053,459 B1
(45) Date of Patent: Nov. 8, 2011

(54) SELENOLOPYRAZOLE DERIVATIVES AND USE THEREOF AS ANTICANCER AGENTS

(75) Inventors: Sheng-Chu Kuo, Taichung (TW); Li-Jiau Huang, Taichung (TW); Li-Chen Chou, Taichung (TW); Jai-Sing Yang, Taichung (TW); Mei-Hua Hsu, Taichung (TW); Shi-Hong Zhuang, Taichung (TW); Mei-Chi Fang, Taichung (TW); Hui-Yi Lin, Taichung (TW)

(73) Assignee: China Medical University, Taichung (TW)

( * ) Notice: Subject to any disclaimer, the term of this patent is extended or adjusted under 35 U.S.C. 154(b) by 0 days.

(21) Appl. No.: 12/805,156

(22) Filed: Jul. 15, 2010

(51) Int. Cl.
*A61K 31/4162* (2006.01)
*C07D 231/54* (2006.01)

(52) U.S. Cl. .......................... 514/405; 548/360.5; 540/1

(58) Field of Classification Search ............... 548/360.5; 514/405

See application file for complete search history.

(56) References Cited

OTHER PUBLICATIONS

European Journal of Medicinal Chemistry 45 (2010) 1395-1402—Jan. 4, 2010.

*Primary Examiner* — Rebecca Anderson
*Assistant Examiner* — Samantha Shterengarts
(74) *Attorney, Agent, or Firm* — Bacon & Thomas, PLLC

(57) ABSTRACT

The present invention synthesizes a series of selenolo[3,2-c]pyrazole and selenolo[2,3-c]pyrazole derivatives, and discovers their anticancer activity.

19 Claims, No Drawings

SELENOLOPYRAZOLE DERIVATIVES AND USE THEREOF AS ANTICANCER AGENTS

FIELD OF THE INVENTION

The present invention is related to a series of novel selenolo[3,2-c]pyrazole and selenolo[2,3-c]pyrazole derivatives, and their use as an anticancer agent.

BACKGROUND OF THE INVENTION

U.S. Pat. No. 7,378,532 B2 discloses novel fused pyrazolyl compounds, and the use thereof in inhibiting cancer cell growth, details of which are incorporated herein by reference.

The inventors of the present application continue their efforts in searching derivatives of the novel fused pyrazolyl compounds disclosed in U.S. Pat. No. 7,378,532 B2, which possess pharmaceutically useful properties.

SUMMARY OF THE INVENTION

An objective of the present invention is to provide novel selenolo[3,2-c]pyrazole and selenolo[2,3-c]pyrazole compounds.

Another objective of the present invention is to provide a pharmaceutical composition for inhibiting cancer cell growth and a method of inhibiting cancer cell growth.

In order to accomplish the aforesaid objectives of the present invention a selenolo[3,2-c]pyrazole and selenolo[2,3-c]pyrazole compound synthesized according to the present invention has a formula of (I) or (II):

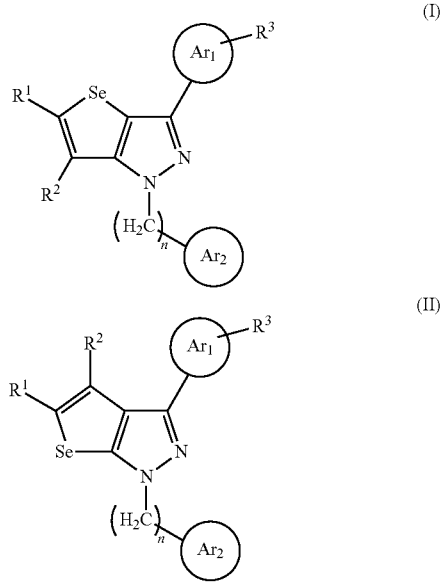

wherein $R^1$ is hydrogen, C1-C6 alkyl, hydroxyl, C1-C6 alkoxyl, F, Cl, or Br;
$R^2$ is hydrogen or methyl;
$R^3$ is —COOR², —(CR²H)$_j$OH, —(CR²H)$_j$—C(O)—(CH$_2$)$_m$—COOH, —(CR²H)$_j$—O—C(O)—(CH$_2$)$_m$—NH$_2$ or —(CR²H)$_j$—O—C(O)—(CH$_2$)$_m$—COOH, wherein $R^2$ is defined as above, j=1-6 and m=1-6;
Ar$_1$ is phenyl or

wherein x is O, S or Se;
Ar$_2$ is

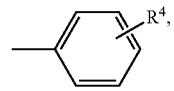

wherein $R^4$ is hydrogen, C1-C6alkyl, hydroxyl, C1-C6 alkoxyl, F, Cl, or Br; and
n=0, 1 or 2.

The present invention also discloses an anticancer pharmaceutical composition comprising a therapeutically effective amount of the compound (I) or (II) as set forth above, or a pharmaceutically acceptable salt thereof, as a potent component.

The present invention further provides a method of inhibiting growth of cancer cells comprising administering the compound (I) or (II) as set forth above, or a pharmaceutically acceptable salt thereof, to a subject suffering said cancer in need of said inhibition.

Preferably, Ar$_1$ is 2-furyl. More preferably, $R^3$ is 5-CH$_2$OH or 5-CH$_2$—O—C(O)—(CH$_2$)$_m$—COOH, wherein m=1 or 2.

Preferably, $R^3$ is 5-CH$_2$OH.
Preferably, $R^3$ is 5-CH$_2$—O—C(O)—(CH$_2$)$_2$—COOH.
Preferably, n=0 or 1. More preferably, $R^2$ and $R^4$ are both hydrogen, and $R^1$ is hydrogen or methyl.
Preferably, the compound has the formula (I).
Preferably, the compound has the formula (II).
Preferably, the cancer is human lung cancer or human renal cancer.

DETAILED DESCRIPTION OF THE INVENTION

In the preferred embodiments of the present invention a series of novel selenolo[3,2-c]pyrazole and selenolo[2,3-c]pyrazole compounds were synthesized, and their potency in inhibiting the proliferation of the human lung cancer cell lines (NCI-H226) and human renal cancer cell lines (A-498) were measured.

The following Scheme 1 shows the reactants and reaction routes to synthesize the intermediate compounds and the final products of the present invention.

Scheme 1

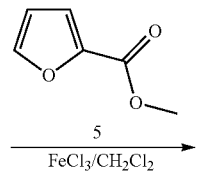

1, R = H
2, R = CH$_3$

3, R = H
4, R = CH$_3$

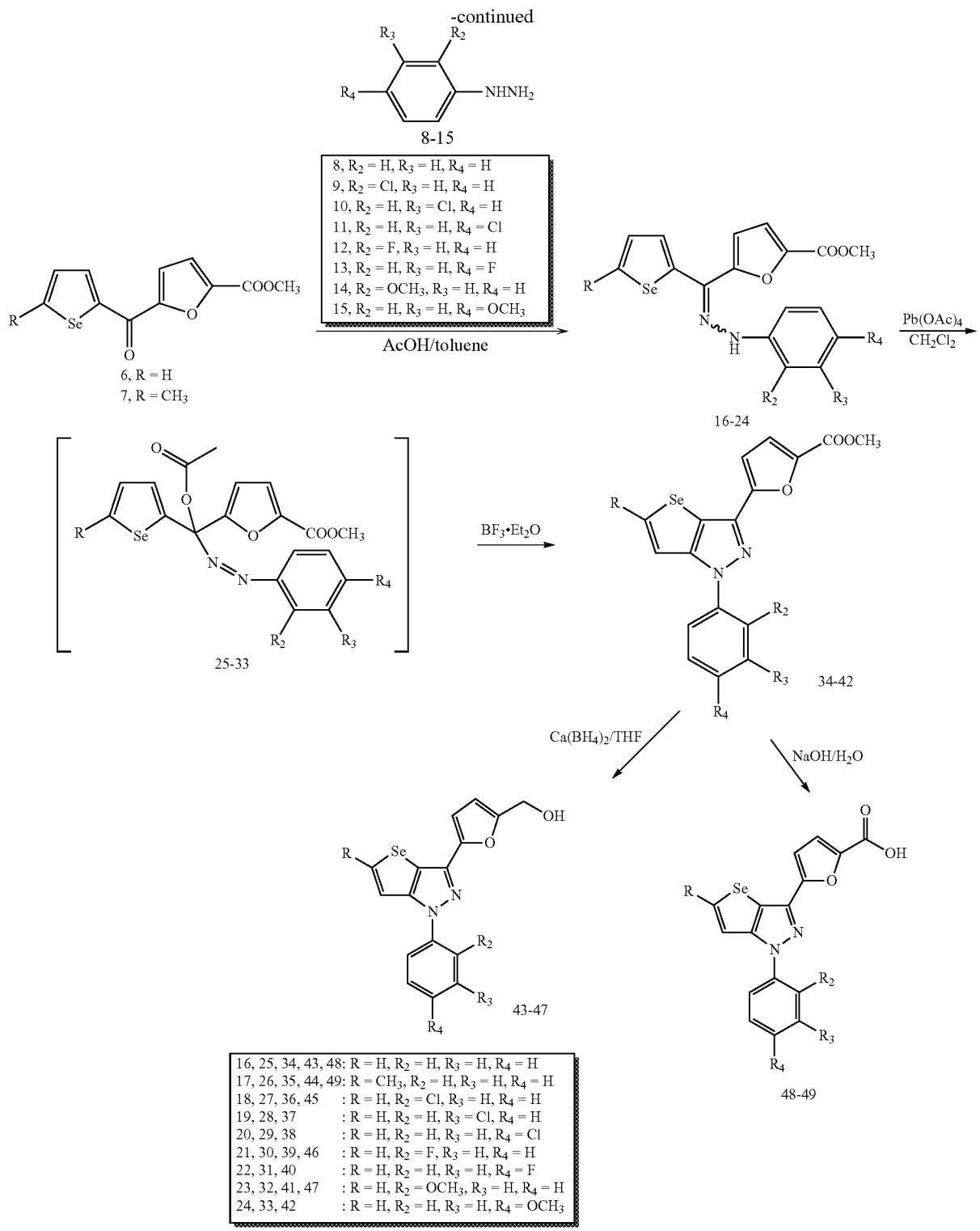

5-Methoxycarbonyl-2-furyl 2-selenophenyl ketone (6)

To selenophene-2-carboxylic acid 1 (5 g, 0.026 mole) in a three-neck flask 50 ml of dichloromethane and 10 g of $SOCl_2$ were added, and the mixture was reacted under refluxing for 20 h. An intermediate compound 3, selenophene-2-carbonyl chloride, was obtained by evaporating $SOCl_2$ under a reduced pressure. Into the intermediate product 3 was added $CH_2Cl_2$ (50 mL), then methyl furan-2-carboxylate (5.4 g) and anhydrous ferric chloride (4.6 g) were added. The reaction mixture was then heated under refluxing for 4 h, cooled and quenched with icewater. The progress of the reaction was monitored by TLC on 2×6 cm pre-coated silica gel 60 $F_{254}$ plates of thickness 0.25 mm (Merck) with dichloromethane:n-hexane=4:1. The CH$_2$Cl$_2$ layer was dried over MgSO$_4$ and filtered. The solvent of the filtrate was evaporated under a reduced pressure, and the residue was subjected to a column chromatography (silica gel 60, Merck, particle size 0.063-0.200 mm) with dichloromethane:n-hexane=4:1, and then recrystallized from dichloromethane to afford compound 6 in white needle crystals (5.0 g). Yield: 62%; mp 115-118° C.

Compound 6:
(1) MS (m/z): 284 (M$^+$)
(2) IR, ν$_{max}$ (KBr) cm$^{-1}$: 1716 (C=O), 1618 (C=O)
(3) UV: λmax (MeOH) nm (log ε): 332 (3.73)
(4) $^1$H-NMR (DMSO-d$_6$, 200 MHz) δ (ppm):
3.84 (s, 3H), 7.44-7.42 (m, 1H), 7.57-7.52 (m, 2H), 8.42-8.40 (m, 1H), 8.78 (d, 1H).
(5) $^{13}$C-NMR (DMSO-d$_6$, 50 MHz) δ (ppm):
52.94, 119.61, 119.96, 132.15, 137.76, 143.91, 146.439, 147.74, 158.41, 174.33.

5-Methoxycarbonyl-2-furyl 5-methyl-2-selenophenyl ketone (7)

Compound 7 was obtained following the synthesis procedures of compound 6 except that 5-methylselenophene-2-carboxylic acid 2 (5 g, 0.026 mole) was used to replace elenophene-2-carboxylic acid 1. White needle crystals. Yield: 3.87 (50%); mp 101-104° C.

Compound 7:
(1) MS (m/z): 298 (M$^+$)
(2) IR, ν$_{max}$(KBr) cm$^{-1}$: 1735 (C=O)
(3) UV: λmax (MeOH) nm (log ε): 317 (3.80)
(4) $^1$H-NMR (DMSO-d$_6$, 200 MHz) δ (ppm):
2.58 (s, 3H), 3.84 (s, 3H), 7.23 (d, 1H), 7.44-7.46 (d, 1H), 7.51-7.52 (d, 1H), 8.24-8.26 (d, 1H).
(5) $^{13}$C-NMR (DMSO-d$_6$, 50 MHz) δ (ppm):
18.96, 52.88, 119.49, 131.23, 138.28, 145.56, 146.23, 152.80, 158.40, 159.89, 173.73.

3-(5-Methoxycarbonyl-2-furyl)-1-phenylselenolo[3,2-c]-pyrazole (34)

Into a solution of compound 6 (3.8 g, 0.013 mole) in toluene (100 ml) was added acetic acid 1.5 ml as a catalyst and phenylhydrazine 8 (5.0 g, 0.046 mole). The mixture was heated under refluxing for 4 h. After cooling, toluene was evaporated and 50 ml of dichloromethane was added to the residue to form a solution (a). 25 g of lead tetraacetate was dissolved in 100 ml of boron trifluoride diethyl etherate to form a solution (b). The solution (a) was quickly poured into the solution (b) in an icewater bath while stirring, and allowed for cyclization reaction for 30 min. The progress of the reaction was monitored by TLC on 2×6 cm pre-coated silica gel 60 F$_{254}$ plates of thickness 0.25 mm (Merck) with dichloromethane:n-hexane=7:1. When the reaction was completed, the reaction mixture was poured into water to stop the reaction, and then was extracted with dichloromethane. The organic layer was recovered, dried over MgSO$_4$ and filtered. The solvent of the filtrate was evaporated under a reduced pressure, and the residue was subjected to a column chromatography (silica gel 60, Merck, particle size 0.063-0.200 mm) with dichloromethane:n-hexane=7:1, and then recrystallized from dichloromethane to afford compound 34 in white needle crystals (0.727 g).
Yield: 14%; mp 144-147° C.

Compound 34:
(1) MS (m/z): 372.0 (M$^+$)
(2) IR, ν$_{max}$ (KBr) cm$^{-1}$: 1724 (C=O)
(3) UV: λmax (MeOH) nm (logs): 326 (4.01)
(4) $^1$H-NMR (DMSO-d$_6$, 200 MHz) δ (ppm):
3.83 (s, 1H), 7.06-7.05 (d, 1H), 7.59-7.37 (m, 4H), 7.84-7.78 (m, 3H), 8.40-8.37 (d, 1H).
(5) $^{13}$C-NMR (DMSO-d$_6$, 50 MHz) δ (ppm):
52.40, 109.32, 114.50, 119.48, 120.86, 127.38, 130.20, 137.64, 139.61, 139.94, 143.71, 149.51, 151.03, 158.63.

3-(5-Methoxycarbonyl-2-furyl)-1-phenyl-5-methylselenolo-[3,2-c]pyrazole (35)

Compound 35 was obtained following the synthesis procedures of compound 34 except that compound 7 (3.8 g, 0.013 mole) was used to replace compound 6. White needle crystals. Yield: 0.486 g (9%); mp 155-157° C.

Compound 35:
(1) MS (m/z): 386 (M$^+$)
(2) IR, ν$_{max}$ (KBr) cm$^{-1}$: 1732 (C=O)
(3) UV: λmax (MeOH) nm (log ε): 329 (4.09)
(4) $^1$H-NMR (DMSO-d$_6$, 200 MHz) δ (ppm):
2.59 (s, 1H), 3.80 (s, 1H), 6.90-6.92 (d, 1H), 7.44-7.37 (m, 2H), 7.76-7.50 (m, 3H), 7.80-7.76 (d, 2H).
(5) $^{13}$C-NMR (DMSO-d$_6$, 50 MHz) δ (ppm):
19.79, 52.36, 109.17, 112.72, 117.30, 120.76, 127.26, 130.11, 137.509, 139.94, 143.61, 148.18, 151.05, 154.29, 158.60.

3-(5-Methoxycarbonyl-2-furyl)-1-(2-chlorophenyl) selenolo-[3,2-c]pyrazole (36)

Compound 36 was obtained following the synthesis procedures of compound 34 except that compound 9 (5 g, 0.035 mole) was used to replace compound 8. White furry crystals. Yield: 0.107 g (2%); mp 134-136° C.

Compound 36:
(1) IR, ν$_{max}$ (KBr) cm$^{-1}$: 1737 (C=O)
(2) UV: λmax (MeOH) nm (log δ): 318 (4.16)
(3) $^1$H-NMR (DMSO-d$_6$, 200 MHz) δ (ppm):
3.81 (s, 1H), 7.03-7.01 (d, 1H), 7.27-7.24 (d, 1H), 7.70-7.42 (m, 5H), 8.32-8.29 (d, 1H).
(4) $^{13}$C-NMR (DMSO-d$_6$, 50 MHz) δ (ppm):
52.42, 109.37, 113.98, 117.59, 119.79, 120.30, 120.81, 128.94, 129.53, 131.04, 132.16, 137.09, 137.09, 137.93, 139.51, 143.70, 150.97, 152.04, 158.64.

3-(5-Methoxycarbonyl-2-furyl)-1-(3-chlorophenyl) selenolo-[3,2-c]pyrazole (37)

Compound 37 was obtained following the synthesis procedures of compound 34 except that compound 10 (5 g, 0.039 mole) was used to replace compound 8. White furry crystals. Yield: 0.107 g (1%); mp 107-109° C.

Compound 37:
(1) IR, ν$_{max}$(KBr) cm$^{-1}$: 1732 (C=O)
(2) UV: λmax (MeOH) nm (log ε): 320 (4.12)
(3) $^1$H-NMR (DMSO-d$_6$, 200 MHz) δ (ppm):
3.81 (s, 3H), 6.98-6.97 (d, 1H), 7.53-7.33 (m, 3H), 7.77-7.70 (m, 3H), 8.37-8.34 (d, 1H).
(4) $^{13}$C-NMR (DMSO-d$_6$, 50 MHz) δ (ppm):
52.36, 109.59, 114.48, 118.87, 120.03, 120.25, 120.64, 126.91, 131.74, 134.52, 138.03, 140.01, 140.93, 143.80, 149.31, 150.65, 158.54.

3-(5-Methoxycarbonyl-2-furyl)-1-(4-chlorophenyl)selenolo-[3,2-c]pyrazole (38)

Compound 38 was obtained following the synthesis procedures of compound 34 except that compound 11 (5 g, 0.039 mole) was used to replace compound 8. White furry crystals. Yield: 0.037 g (1%); mp 146-148° C.

Compound 38:
(1) IR, $v_{max}$ (KBr) cm$^{-1}$: 1728 (C=O)
(2) UV: λmax (MeOH) nm (log ε): 322 (4.17)
(3) $^1$H-NMR (DMSO-d$_6$, 200 MHz) δ (ppm):
3.82 (s, 1H), 7.04-7.03 (d, 1H), 7.43-7.41 (d, 1H), 7.58-7.54 (d, 2H), 7.85-7.77 (m, 3H), 8.40-8.38 (d, 1H).
(4) $^{13}$C-NMR (DMSO-d$_6$, 200 MHz) δ (ppm):
52.40, 109.50, 114.45, 119.82, 120.72, 122.21, 130.03, 131.32, 137.85, 138.66, 139.94, 143.77, 149.36, 150.76, 158.58

3-(5-Methoxycarbonyl-2-furyl)-1-(2-fluorophenyl)selenolo-[3,2-c]pyrazole (39)

Compound 36 was obtained following the synthesis procedures of compound 34 except that compound 12 (5 g, 0.039 mole) was used to replace compound 8. White furry crystals. Yield: 0.085 g (4%); mp 158-161° C.

Compound 39:
(1) IR, $v_{max}$ (KBr) cm$^{-1}$: 1712 (C=O)
(2) UV: λmax (MeOH) nm (log ε): 322 (4.12)
(3) $^1$H-NMR (DMSO-d$_6$, 200 MHz) δ (ppm):
3.81 (s, 3H), 7.04-7.02 (d, 1H), 7.54-7.36 (m, 5H), 7.73 (t, 1H), 8.34-8.31 (d, 1H).
(4) $^{13}$C-NMR (DMSO-d$_6$, 200 MHz) δ (ppm):
52.43, 109.53, 114.17, 117.38, 117.76, 118.25, 120.83, 126.02, 127.47, 130.64, 130.79, 138.38, 139.68, 143.80, 150.84, 151.71, 158.63.

3-(5-Methoxycarbonyl-2-furyl)-1-(4-fluorophenyl)selenolo-[3,2-c]pyrazole (40)

Compound 36 was obtained following the synthesis procedures of compound 34 except that compound 13 (5 g, 0.039 mole) was used to replace compound 8. White furry crystals. Yield: 0.063 g (3%); mp 160-163° C.

Compound 40:
(1) IR, $v_{max}$ (KBr) cm$^{-1}$: 1707 (C=O)
(2) UV: λmax (MeOH) nm (log ε): 300 (4.09)
(3) $^1$H-NMR (DMSO-d$_6$, 200 MHz) δ (ppm):
3.82 (s, 3H), 7.04-7.02 (d, 1H), 7.44-7.32 (m, 3H), 7.87-7.70 (m, 2H), 8.39-8.36 (d, 1H).
(4) $^{13}$C-NMR (DMSO-d$_6$, 200 MHz) δ (ppm):
52.41, 109.37, 114.31, 116.74, 117.20, 120.80, 123.04, 123.21, 136.41, 137.64, 139.81, 143.72, 149.62, 150.93, 158.61.

3-(5-Methoxycarbonyl-2-furyl)-1-(2-methoxyphenyl)selenolo-[3,2-c]pyrazole (41)

Compound 41 was obtained following the synthesis procedures of compound 34 except that compound 14 (5 g, 0.039 mole) was used to replace compound 8. Viscous liquid. Yield: 0.037 g (1%); mp 72-76° C.

Compound 41:
(1) IR, $v_{max}$ (KBr) cm$^{-1}$: 1716 (C=O)
(2) UV: λmax (MeOH) nm (log ε): 320 (4.22)
(3) $^1$H-NMR (DMSO d$_6$, 200 MHz) δ (ppm):
3.78 (s, 3H), 3.81 (s, 3H), 6.99-6.97. (d, 1H), 7.28-7.08 (m, 3H), 7.51-7.42 (m, 3H), 8.24-8.21 (d, 1H).
(4) $^{13}$C-NMR (DMSO-d$_6$, 50 MHz) δ (ppm):
52.37, 56.21, 108.92, 113.33, 114.92, 120.85, 121.28, 127.58, 128.48, 130.46, 137.40, 138.13, 143.52, 151.39, 152.17, 153.12, 158.68.

3-(5-Methoxycarbonyl-2-furyl)-1-(4-methoxyphenyl)selenolo-[3,2-c]pyrazole (42)

Compound 42 was obtained following the synthesis procedures of compound 34 except that compound 15 (5 g, 0.039 mole) was used to replace compound 8. Viscous liquid. Yield: 0.028 g (1%); mp 89-92° C.

Compound 42:
(1) IR, $v_{max}$ (KBr) cm$^{-1}$: 1721 (C=O)
(2) UV: λmax (MeOH) nm (log ε): 316 (4.25)
(3) $^1$H-NMR (DMSO-d$_6$, 200 MHz) δ (ppm):
3.77 (s, 3H), 3.86-3.81 (m, 3H), 7.01-6.96 (m, 2H), 7.56-7.46 (m, 2H), 7.78-7.67 (m, 3H), 8.41-8.39 (m, 1H).

3-(5-Hydroxymethyl-2-furyl)-1-phenylselenolo[3,2-c]pyrazole (43)

Anhydrous tetrahydrofuran (THF) was prepared by heating THF over sodium under refluxing, wherein benzophenone was used as an indicator. The heating was stop until the solvent became deep blue.

7.5 g (0.068 mole) of granular anhydrous calcium chloride, 5.0 g (0.132 mole) of sodium brorhydride and 100 ml of anhydrous THF were reacted at room temperature for 4 h to form a white dispersion of calcium borohydride (Ca(BH$_4$)$_2$). To the dispersion compound 34 (3 g, 0.008 mole) was added and was reduced by heating under refluxing for 24 h. The progress of the reduction reaction was monitored by TLC with ethyl acetate (EA):n-hexane=3:2. When the reaction was completed, the reaction mixture was cooled to room temperature, and THF was evaporated under a reduced pressure. The remaining reaction mixture was poured into water to stop the reaction, and then was extracted with chloroform. The organic layer was recovered, dried over MgSO$_4$ and filtered. The solvent of the filtrate was evaporated under a reduced pressure, and the residue was subjected to a column chromatography with EA:n-hexane=3:2, and then recrystallized from EA to afford compound 43 in viscous liquid (2.09 g). Yield: 72%.

Compound 43:
(1) MS (m/z): 344.1 (M$^+$)
(2) IR, $v_{max}$ (KBr) cm$^{-1}$: 3100-3500 (OH)
(3) UV: λmax (MeOH) nm (log ε): 262 (4.19), 318 (4.11)
(4) $^1$H-NMR (DMSO-d$_6$, 200 MHz) δ (ppm)):
4.47-4.45 (d, 2H), 5.34 (t, 1H), 6.46-6.45 (d, 1H), 6.79-6.77 (d, 1H), 7.37-7.33 (m, 1H), 7.57-7.49 (m, 2H), 7.82-7.77 (m, 3H), 8.37-8.34 (d, 1H).
(5) $^{13}$C-NMR (DMSO-d$_6$, 50 MHz) δ (ppm):
56.18, 108.47, 109.72, 114.60, 118.63, 120.46, 126.88, 130.17, 138.87, 139.10, 140.17, 146.61, 149.11, 156.44.

3-(5-Hydroxymethyl-2-furyl)-1-5-methyl-phenylselenolo[3,2-c]pyrazole (44)

Compound 44 was obtained following the synthesis procedures of compound 43 except that compound 35 (3 g, 0.008 mole) was used to replace compound 34. Viscous liquid. Yield: 1.916 g (66%).

Compound 44:
(1) MS (m/z): 356 (M+)
(2) IR, $v_{max}$ (KBr) cm$^{-1}$: 3200-3400 (OH)
(3) UV: λmax (MeOH) nm (log ε): 266 (4.25), 318 (4.30)
(4) $^1$H-NMR (DMSO-d$_6$, 200 MHz) δ (ppm):
2.62 (s, 3H), 4.46-4.43 (d, 2H), 5.35-5.30 (t, 1H), 6.45-6.43 (d, 1H), 6.73-6.71 (d, 1H), 7.35-7.32 (t, 1H), 7.74-7.51 (m, 3H), 7.79-7.74 (d, 2H).
(5) $^{13}$C-NMR (DMSO-d$_6$, 50 MHz) δ (ppm):
19.87, 56.15, 108.39, 109.66, 112.92, 126.81, 120.42, 130.13, 140.18, 146.61, 147.82, 153.809, 156.30.

3-(5-Hydroxymethyl-2-furyl)-1-(2-chlorophenyl) selenolo[3,2-c]pyrazole (45)

Compound 45 was obtained following the synthesis procedures of compound 43 except that compound 36 (3 g, 0.0077 mole) was used to replace compound 34. Furry crystals. Yield: 0.04 g (71%).
Compound 45:
(1) IR, $v_{max}$(KBr) cm$^{-1}$: 3100-3500 (OH)
(2) UV: λmax (MeOH) nm (log ε): 310 (4.08)
(3) $^1$H-NMR (DMSO-d$_6$, 200 MHz) δ (ppm):
46-4.43 (d, 1H), 5.33 (t, 1H), 6.45-6.43 (d, 1H), 6.75-6.73 (d, 1H), 7.23-7.20 (d, 1H), 7.55-7.23 (m, 2H), 7.73-7.62 (m, 2H), 8.28-8.25 (d, 1H).
(4) $^{13}$C-NMR (DMSO-d$_6$, 50 MHz) δ (ppm):
56.16, 108.35, 109.65, 114.07, 116.71, 128.86, 129.46, 131.02, 137.37, 138.80, 139.16, 146.60, 151.63, 156.35.

3-(5-Hydroxymethyl-2-furyl)-1-(2-fluorophenyl) selenolo[3,2-c]pyrazole (46)

Compound 46 was obtained following the synthesis procedures of compound 43 except that compound 39 (3 g, 0.008 mole) was used to replace compound 34. Furry crystals. Yield: 0.025 g (69%); mp: 178-181° C.
Compound 46:
(1) IR, $v_{max}$ (KBr) cm$^{-1}$: 3100-3500 (OH)
(2) UV: λmax (MeOH) nm (log ε): 322 (4.06)
(3) $^1$H-NMR (DMSO-d$_6$, 200 MHz) δ (ppm):
4.48 (d, 1H), 5.37 (t, 1H), 6.46 (d, 1H), 6.77 (d, 1H), 7.47-7.35 (m, 4H), 7.70 (t, 1H), 8.30-8.28 (d, 1H).
(4) $^{13}$C-NMR (DMSO-d$_6$, 50 MHz) δ (ppm):
56.18, 108.58, 109.68, 114.13, 114.24, 117.30, 117.42, 117.69, 125.91, 127.22, 130.07, 130.23, 138.94, 39.61, 146.48, 151.26, 152.50, 156.50, 157.46.

3-(5-Hydroxymethyl-2-furyl)-1-(2-methoxyphenyl) selenolo[3,2-c]pyrazole (47)

Compound 47 was obtained following the synthesis procedures of compound 43 except that compound 41 (3 g, 0.008 mole) was used to replace compound 34. Yield: 0.033 g (70%).
Compound 47:
(1) IR, $v_{max}$ (KBr) cm$^{-1}$: 3100-3500 (OH)
(2) UV: λ max (MeOH) nm (log ε): 312 (4.27)
(3) $^1$H-NMR (DMSO-d$_6$, 200 MHz) δ (ppm):
3.78 (s, 3H), 4.45 (s, 2H), 6.43 (d, 1H), 6.70 (d, 1H), 7.26-7.07 (m, 3H), 7.45-7.39 (m, 2H), 8.19-8.17 (d, 1H).
(4) $^{13}$C-NMR (DMSO-d$_6$, 50 MHz) δ (ppm):
56.15, 107.85, 109.60, 113.24, 115.05, 116.26, 121.23, 127.42, 128.77, 129.98, 137.43, 138.61, 146.94, 151.72, 152.96, 156.09.

3-(5-Hydroxycarbonyl-2-furyl)-1-phenylselenolo[3,2-c]pyrazole (48)

Compound 34 (1.49 g, 0.004 mole) in 40 ml of 10% NaOH solution was heated under refluxing for 2 h. The progress of the hydrolysis reaction was monitored by TLC with ethyl acetate (EA). When the reaction was completed, the reaction mixture was poured into water to stop the reaction, and then was extracted with toluene. The aqueous layer was recovered, and acidified with 10% HCl solution, which was then extracted with EA. The organic layer was recovered and dried over MgSO$_4$ and filtered. The solvent of the filtrate was evaporated under a reduced pressure, and the residue was then recrystallized from EA to afford compound 48 in brown columnar crystals (0.76 g). Yield: 78%; mp 234-237° C.
Compound 48:
(1) MS (m/z): 358 (M+)
(2) IR, $v_{max}$ (KBr) cm$^{-1}$: 1673 (C=O), 2400-3200 (OH)
(3) UV: λmax (MeOH) nm (log ε): 316 (4.19)
(4) $^1$H-NMR (DMSO-d$_6$, 200 MHz) δ0 (ppm):
3.41 (br, 1H), 7.03-7.02 (d, 1H), 7.36-7.34 (m, 2H), 7.58-7.51 (t, 2H), 7.83-7.79 (d, 3H), 8.40-8.37 (d, 1H).
(5) $^{13}$C-NMR (DMSO-d$_6$, 50 MHz) δ (ppm):
109.19, 114.52, 119.39, 120.20, 120.83, 127.35, 130.21, 137.86, 139.59, 139.97, 144.96, 149.49, 150.58, 159.61.

3-(5-Hydroxycarbonyl-2-furyl)-1-phenyl-5-methylselenolo[3,2-c]pyrazole (49)

Compound 49 was obtained following the synthesis procedures of compound 48 except that compound 35 (1.49 g, 0.004 mole) was used to replace compound 34. Yield: 1.098 g (73%); mp 236-239° C.
Compound 49:
(1) MS (m/z): 372.1 (M+)
(2) IR, $v_{max}$ (KBr) cm$^{-1}$: 1671 (C=O), 2400-3200 (OH)
(3) UV: λmax (MeOH) nm (log ε): 326 (4.19)
(4) $^1$H-NMR (DMSO-d$_6$, 200 MHz) δ (ppm):
2.63 (s, 3H), 3.65 (br, 1H), 6.96-6.94 (d, 1H), 7.34-7.32 (m, 2H), 7.35 (s, 1H), 7.56-7.48 (m, 3H), 7.79-7.75 (d, 2H)
(5) $^{13}$C-NMR (DMSO-d$_6$, 50 MHz) δ (ppm):
19.84, 109.14, 112.78, 117.19, 120.21, 120.79, 130.19, 127.31, 137.75, 139.95, 144.87, 148.22, 150.57, 154.399, 159.62.

The following Scheme 2 shows the reactants and reaction routes to synthesize the intermediate compounds and the compounds 55-60 of the present invention.

Scheme 2

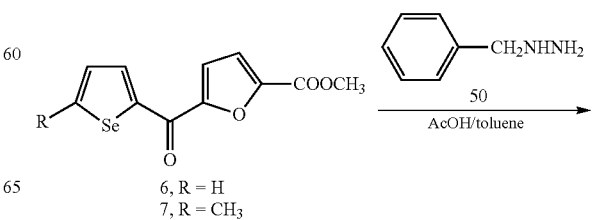

6, R = H
7, R = CH$_3$

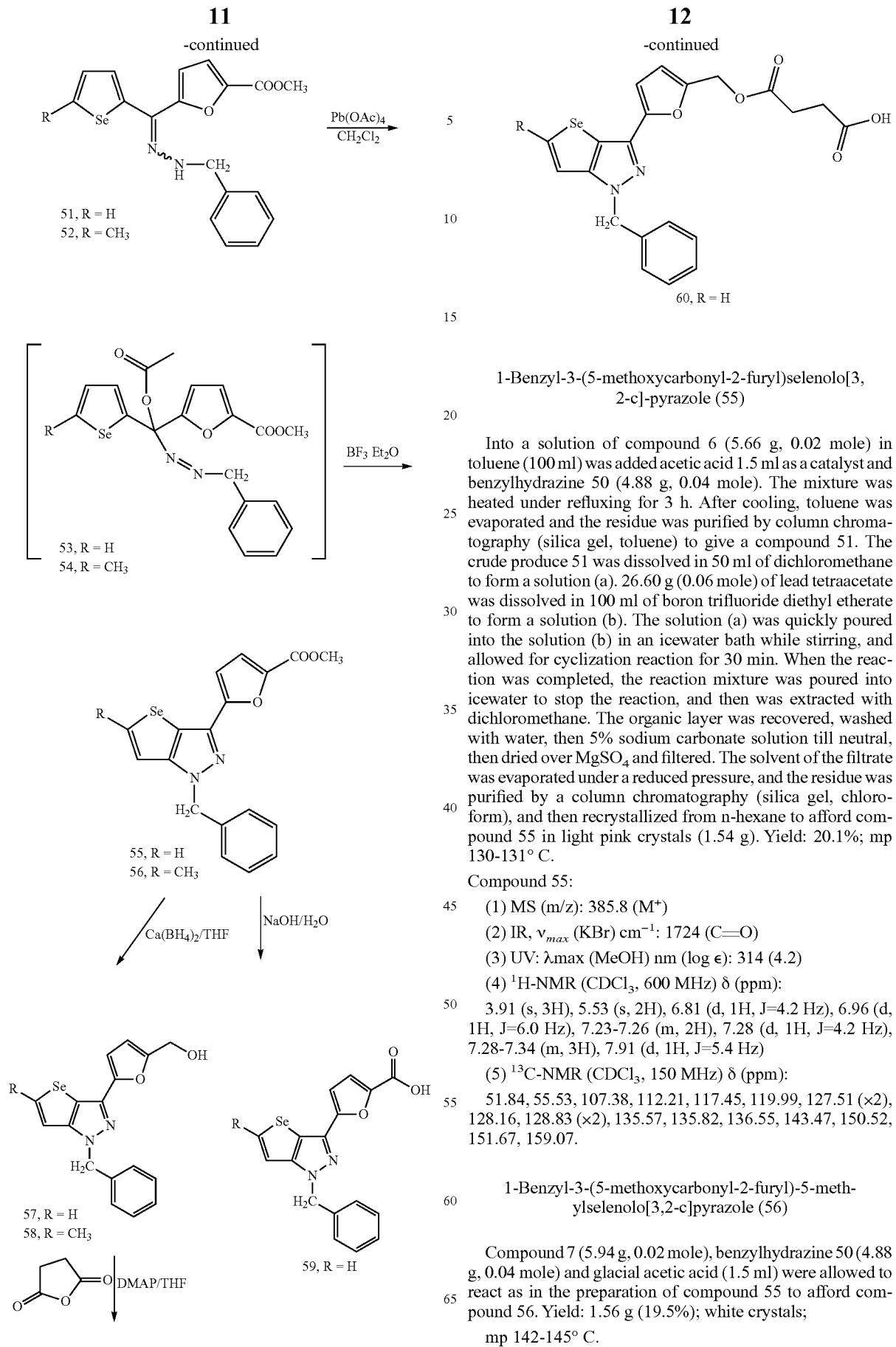

1-Benzyl-3-(5-methoxycarbonyl-2-furyl)selenolo[3,2-c]-pyrazole (55)

Into a solution of compound 6 (5.66 g, 0.02 mole) in toluene (100 ml) was added acetic acid 1.5 ml as a catalyst and benzylhydrazine 50 (4.88 g, 0.04 mole). The mixture was heated under refluxing for 3 h. After cooling, toluene was evaporated and the residue was purified by column chromatography (silica gel, toluene) to give a compound 51. The crude produce 51 was dissolved in 50 ml of dichloromethane to form a solution (a). 26.60 g (0.06 mole) of lead tetraacetate was dissolved in 100 ml of boron trifluoride diethyl etherate to form a solution (b). The solution (a) was quickly poured into the solution (b) in an icewater bath while stirring, and allowed for cyclization reaction for 30 min. When the reaction was completed, the reaction mixture was poured into icewater to stop the reaction, and then was extracted with dichloromethane. The organic layer was recovered, washed with water, then 5% sodium carbonate solution till neutral, then dried over MgSO$_4$ and filtered. The solvent of the filtrate was evaporated under a reduced pressure, and the residue was purified by a column chromatography (silica gel, chloroform), and then recrystallized from n-hexane to afford compound 55 in light pink crystals (1.54 g). Yield: 20.1%; mp 130-131° C.

Compound 55:

(1) MS (m/z): 385.8 (M$^+$)

(2) IR, $\nu_{max}$ (KBr) cm$^{-1}$: 1724 (C=O)

(3) UV: λmax (MeOH) nm (log ϵ): 314 (4.2)

(4) $^1$H-NMR (CDCl$_3$, 600 MHz) δ (ppm):

3.91 (s, 3H), 5.53 (s, 2H), 6.81 (d, 1H, J=4.2 Hz), 6.96 (d, 1H, J=6.0 Hz), 7.23-7.26 (m, 2H), 7.28 (d, 1H, J=4.2 Hz), 7.28-7.34 (m, 3H), 7.91 (d, 1H, J=5.4 Hz)

(5) $^{13}$C-NMR (CDCl$_3$, 150 MHz) δ (ppm):

51.84, 55.53, 107.38, 112.21, 117.45, 119.99, 127.51 (×2), 128.16, 128.83 (×2), 135.57, 135.82, 136.55, 143.47, 150.52, 151.67, 159.07.

1-Benzyl-3-(5-methoxycarbonyl-2-furyl)-5-methylselenolo[3,2-c]pyrazole (56)

Compound 7 (5.94 g, 0.02 mole), benzylhydrazine 50 (4.88 g, 0.04 mole) and glacial acetic acid (1.5 ml) were allowed to react as in the preparation of compound 55 to afford compound 56. Yield: 1.56 g (19.5%); white crystals;

mp 142-145° C.

Compound 56:
(1) MS (m/z): 400.1 (M$^+$)
(2) IR, $\nu_{max}$(KBr) cm$^{-1}$: 1730 (C=O)
(3) UV: λmax (MeOH) nm (log ε): 314 (3.4)
(4) $^1$H-NMR (CDCl$_3$, 200 MHz) δ (ppm):
2.56 (s, 3H), 3.89 (s, 3H), 5.46 (s, 2H), 6.62 (s, 1H), 7.76 (d, 1H, J=3.6 Hz), 7.18-7.32 (m, 6H)
(5) $^{13}$C-NMR (CDCl$_3$, 50 MHz) δ (ppm):
19.68, 51.84, 55.34, 107.46, 110.09, 115.72, 120.02, 127.43, 128.10, 128.84, 136.01, 136.46, 143.45, 149.57, 151.75, 152.52, 159.12.

1-Benzyl-3-(5-hydroxymethyl-2-furyl)selenolo[3,2-c]pyrazole (57)

1.98 g (0.018 mole) of anhydrous calcium chloride, 1.377 g (0.036 mole) of sodium brorhydride and 50 ml of anhydrous THF were reacted at room temperature for 4 h to form a dispersion of calcium borohydride (Ca(BH$_4$)$_2$). To the dispersion compound 55 (0.772 g, 0.002 mole) was added and was heated under refluxing for 6 h. When the reaction was completed, the reaction mixture was poured into icewater to stop the reaction, and then was extracted with dichloromethane. The organic layer was recovered, dried over MgSO$_4$ and filtered. The solvent of the filtrate was evaporated under a reduced pressure, and the residue was subjected to a column chromatography (silica gel, EA:n-hexane=1:1), and then recrystallized from n-hexane to afford compound 57 in pink columnar crystals (0.530 g). Yield: 74.2%; mp 126-129° C.

Compound 57:
(1) MS (m/z): 358 (M$^+$)
(2) IR, $\nu_{max}$ (KBr) cm$^{-1}$: 3200-3400 (OH)
(3) UV: λmax (MeOH) nm (log ε): 303 (3.8)
(4) $^1$H-NMR (CDCl$_3$, 200 MHz) δ (ppm):
4.41 (d, 2H, J=5.6 Hz), 5.29 (t, 1H, J=5.6 Hz), 5.53 (s, 2H), 6.38 (d, 1H, J=3.0 Hz), 6.59 (d, 1H, J=3.0 Hz), 7.25-7.33 (m, 5H), 7.48 (d, 1H, J=5.8 Hz), 8.11 (d, 1H, J=5.8 Hz)
(5) $^{13}$C-NMR (CDCl$_3$, 50 MHz) δ (ppm):
54.46, 56.11, 107.11, 109.49, 113.53, 115.37, 127.99, 128.19, 129.09, 137.22, 137.62, 147.28, 151.24, 155.68.

1-Benzyl-3-(5-hydroxymethyl-2-furyl)-5-methylselenolo[3,2-c]pyrazole (58)

Compound 56 (0.800 g, 0.002 mole) was used to replace compound 55 in the preparation of compound 57 to afford compound 58. Yield: 0.612 g (82.5%); white needle crystals; mp 147-148° C.

Compound 58:
(1) MS (m/z): 372.1 (M$^+$)
(2) IR, $\nu_{max}$ (KBr) cm$^{-1}$: 3200-3400 (OH)
(3) UV: λmax (MeOH) nm (log ε): 262 (3.6)
(4) $^1$H-NMR (CDCl$_3$, 200 MHz) δ (ppm):
2.54 (s, 3H), 4.39 (d, 2H, J=3.6 Hz), 5.27 (t, 1H, J=3.6 Hz), 5.46 (s, 2H), 6.36 (d, 1H, J=3.0 Hz), 6.54 (d, 1H, J=3.0 Hz), 7.19-7.33 (m, 6H)
(5) $^{13}$C-NMR (CDCl$_3$, 50 MHz) δ (ppm):
19.78, 54.36, 56.09, 107.05, 109.45, 111.56, 113.32, 127.90, 128.16, 129.09, 137.14, 137.66, 147.28, 149.90, 151.90, 155.59.

1-Benzyl-3-(5-hydroxycarbonyl-2-furyl)selenolo[3,2-c]pyrazole (59)

Compound 55 (0.772 g, 0.002 mole) in 20 ml of 10% NaOH solution was heated under refluxing for 2 h, cooled and acidified with 10% HCl solution in an icewater bath. The precipitates were collected, then recrystallized from ethanol to afford compound 59 (0.595 g). Yield 80.2%; white crystals; mp 243-244° C.

Compound 59
(1) MS (m/z): 372.0 (M$^+$)
(2) IR, $\nu_{max}$ (KBr) cm$^{-1}$: 1697 (C=O); 2500-3400 (OH)
(3) UV: λmax (MeOH) nm (log ε): 310 (4.2)
(4) $^1$H-NMR (CDCl$_3$, 200 MHz) δ (ppm):
5.58 (s, 2H), 6.82 (d, 1H, J=3.6 Hz), 7.18-7.35 (m, 6H), 7.52 (d, 1H, J=5.6 Hz), 8.18 (d, 1H, J=5.6 Hz)
(5) $^{13}$C-NMR (CDCl$_3$, 50 MHz) δ (ppm):
54.69, 108.03, 113.52, 116.44, 119.55, 128.07, 128.29, 129.13, 136.37, 137.33, 137.75, 145.30, 150.86, 151.51, 160.03.

Succinic Acid mono-[5-(1-benzyl-selenolo[3,2-c]pyrazol-3-yl)furan-2-yl]methyl ester (60)

Compound 57 (1.071 g, 0.003 mole), succinic acid (0.9 g, 0.009 mole) and 4-dimethylaminopyridine (DMAP) (0.403 g, 0.0033 mole) were dissolved in 75 ml of THF in a three-neck flask, and heated under refluxing for 2 h. Water was then introduced into the flask to stop the reaction, and then THF was evaporated. The aqueous layer was acidified by adding 10% HCl solution till pH=2, and then extracted with ethyl acetate (EA). The organic layer was dried over MgSO$_4$ and filtered. The solvent of the filtrate was evaporated under a reduced pressure, and the residue was subjected to a column chromatography (silica gel, EA), and then recrystallized from EA/n-hexane to afford compound 60 in white crystals (0.548 g). Yield: 40%;
mp 111-114° C.

Compound 60:
(1) MS (m/z): 457 (M$^+$)
(2) IR, $\nu_{max}$ (KBr) cm$^{-1}$: 1717 (C=O); 2700-3300 (OH)
(3) UV: λmax (MeOH) nm (log ε): 303 (3.9)
(4) $^1$H-NMR (CDCl$_3$, 200 MHz) δ (ppm):
2.40-2.48 (m, 4H), 5.09 (s, 2H), 5.55 (s, 2H), 6.61 (d, 1H, J=3.4 Hz), 6.66 (d, 1H, J=3.4 Hz), 7.18-7.33 (m, 5H), 7.48 (d, 1H, J=5.8 Hz), 8.15 (d, 1H, J=5.8 Hz)
(5) $^{13}$C-NMR (CDCl$_3$, 50 MHz) δ (ppm):
29.09, 54.54, 58.18, 107.27, 113.24, 113.51, 115.74, 127.97, 128.20, 129.09, 136.87, 137.37, 137.52, 148.54, 149.44, 151.33, 172.30, 173.73.

The following Scheme 3 shows the reactants and reaction routes to synthesize the intermediate compounds and the compounds 66-70 of the present invention.

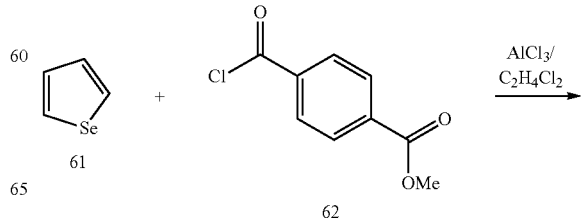

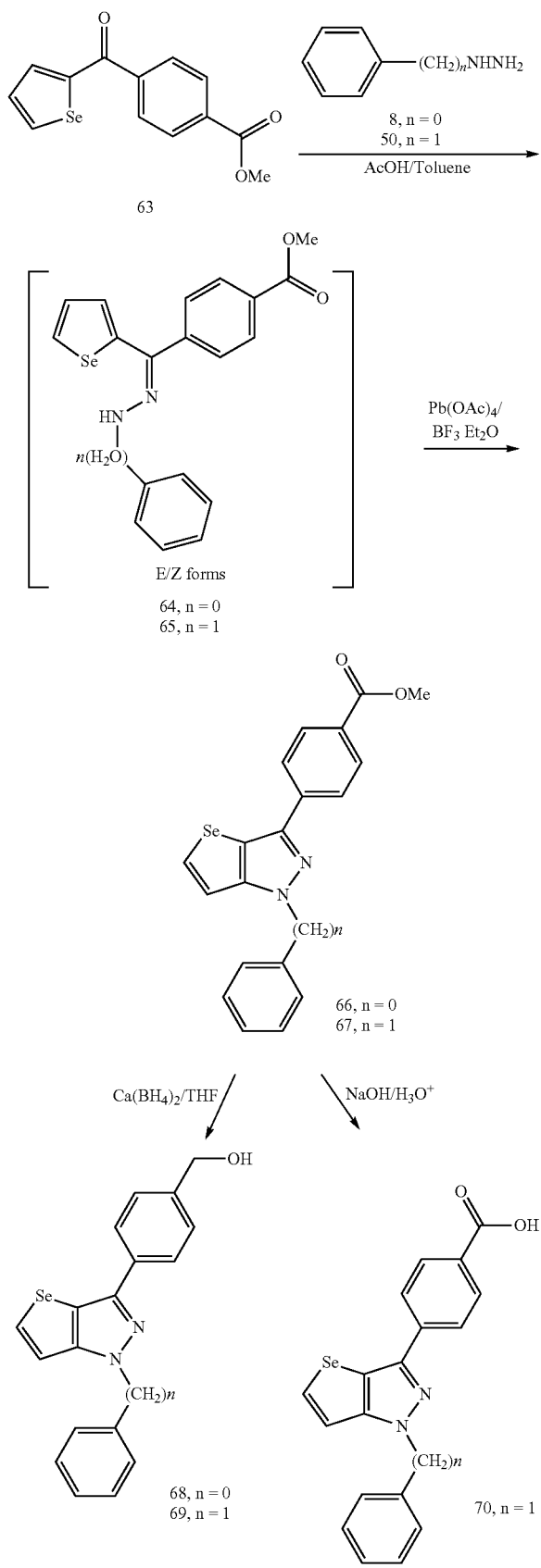

p-Methoxycarbonylphenyl 2-selenophenyl ketone (63)

Selenophene (61) (5.0 g, 0.038 mole) and 4-methoxycarbonyl benzoyl chloride (62) (8.34 g, 0.042 mole) were dissolved in 50 ml of 1, 2-dichloroethane, and then anhydrous aluminum chloride ($AlCl_3$) (10.19 g, 0.076 mole) was added. The mixture was heated under refluxing for 30 min, cooled, and quenched with 250 ml of icewater to stop the reaction. The organic layer was sequentially washed with water, 5% sodium carbonate solution, and water till neutral, then dried over $MgSO_4$ and filtered. The solvent of the filtrate was evaporated under a reduced pressure, and the residue was subjected to a column chromatography (silica gel, chloroform), and then recrystallized from n-hexane to afford compound 63 in yellow crystals (4.78 g).
Yield: 43%; mp 124-127° C.
Compound 63:
(1) MS (m/z): 294.0 ($M^+$)
(2) IR, $\nu_{max}$ (KBr) $cm^{-1}$: 1618, 1715 (C=O)
(3) $^1$H-NMR ($CDCl_3$, 200 MHz) δ (ppm):
3.94 (s, 3H), 7.41 (dd, 1H, J=4.0, 5.4 Hz), 7.79 (d, 1H, J=4.0 Hz); 7.85 (d, 2H, J=8.6 Hz), 8.13 (d, 2H, J=8.6 Hz); 8.47 (d, 1H, J=5.4 Hz)
(4) $^{13}$C-NMR ($CDCl_3$, 50 MHz) δ (ppm):
52.46, 128.95, 129.63, 130.89, 133.06, 137.77, 141.23, 141.51, 150.01, 166.29, 188.77.

1-Phenyl-3-(p-methoxycarbonylphenyl)selenolo[3,2-c]pyrazole (66)

Compound 63 (5.86 g, 0.02 mole), phenylhydrazine 8 (4.36 g, 0.04 mole) and glacial acetic acid (1.5 ml) were allowed to react as in the preparation of compound 55 to afford compound 66. Yield: 1.93 g (25.3%); white crystals; mp 165-166° C.
Compound 66:
(1) MS (m/z): 382 ($M^+$)
(2) IR, $\nu_{max}$ (KBr) $cm^{-1}$: 1713 (C=O)
(3) $^1$H-NMR (DMSO-$d_6$, 200 MHz) δ (ppm):
3.85 (d, 3H), 7.37 (t, 1H, J=7.2 Hz), 7.56 (t, 2H, J=8.2 Hz), 7.81-7.89 (m, 3H), 7.95-8.11 (m, 4H), 8.40 (d, 1H, J=5.8 Hz)
(4) $^{13}$C-NMR (DMSO-$d_6$, 50 MHz) δ (ppm):
52.67, 114.64, 119.47, 120.84, 125.99, 127.27, 129.45, 130.23, 130.57, 136.57, 139.25, 140.13, 144.47, 149.93, 166.36

1-Benzyl-3-(p-methoxycarbonylphenyl)selenolo[3,2-c]pyrazole (67)

Compound 63 (5.86 g, 0.02 mole), benzylhydrazine 50 (4.88 g, 0.04 mole) and glacial acetic acid (1.5 ml) were allowed to react as in the preparation of compound 55 to afford compound 67. Yield: 2.49 g (31.4%); white crystals; mp 150-153° C.
Compound 67:
(1) MS (m/z): 396.0 ($M^+$)
(2) IR, $\nu_{max}$ (KBr) $cm^{-1}$: 1717 (C=O)
(3) UV: λmax (MeOH) nm (log ε): 310 (3.8)
(4) $^1$H-NMR ($CDCl_3$, 200 MHz) δ (ppm):
3.91 (s, 3H), 5.53 (s, 2H), 7.00 (d, 1H, J=5.8 Hz), 7.21-7.38 (m, 5H), 7.85-7.95 (m, 3H), 8.10 (d, 2H, J=8.6 Hz)
(5) $^{13}$C-NMR ($CDCl_3$, 50 MHz) δ (ppm):
52.12, 55.48, 112.51, 117.20, 125.41, 127.52, 128.13, 128.86, 130.16, 134.83, 136.12, 137.11, 143.55, 150.91, 166.95.

1-Phenyl-3-(p-hydroxymethylphenyl)selenolo[3,2-c]pyrazole (68)

Compound 66 (0.764 g, 0.002 mole) was used to replace compound 55 in the preparation of compound 57 to afford compound 68. Yield: 0.585 g (82.9%); white needle crystals; mp 133-134° C.

Compound 68:
(1) MS (m/z): 354 (M$^+$)
(2) IR, $\nu_{max}$ (KBr) cm$^{-1}$: 3100-3500 (OH)
(3) $^1$H-NMR (DMSO-d$_6$, 200 MHz) δ (ppm):
4.53 (d, 2H, J=5.8 Hz), 5.28 (t, 1H, J=5.8 Hz), 7.34 (t, 1H, J=7.0 Hz), 7.45 (d, 2H, J=8.0 Hz), 7.55 (t, 2H, J=8.0 Hz), 7.79-7.86 (m, 5H), 8.37 (d, 1H, J=5.8 Hz)
(4) $^{13}$C-NMR (DMSO-d$_6$, 50 MHz) δ (ppm):
63.13, 114.70, 118.89, 120.53, 125.70, 126.84, 127.61, 130.17, 130.65, 138.72, 140.31, 143.34, 145.59, 149.55

1-Benzyl-3-(p-hydroxymethylphenyl)selenolo[3,2-c]pyrazole (69)

Compound 67 (0.792 g, 0.002 mole) was used to replace compound 55 in the preparation of compound 57 to afford compound 69. Yield: 0.564 g (76.8%); white needle crystals; mp 158-160° C.

Compound 69:
(1) MS (m/z): 368.1 (M$^+$)
(2) IR, $\nu_{max}$ (KBr) cm$^{-1}$: 3100-3500 (OH)
(3) UV: $\lambda_{max}$(MeOH) nm (log ε): 292 (3.9)
(4) $^1$H-NMR (CDCl$_3$, 200 MHz) δ (ppm):
4.49 (d, 2H, J=5.2 Hz), 5.21 (t, 1H, J=5.2 Hz), 5.56 (s, 2H), 7.20-7.33 (m, 5H), 7.39 (d, 2H, J=8.0 Hz), 7.51 (d, 1H, J=5.8 Hz), 7.68 (d, 2H, J=8.2 Hz), 8.16 (d, 1H, J=5.8 Hz)
(5) $^{13}$C-NMR (CDCl$_3$, 50 MHz) δ (ppm):
54.49, 63.12, 113.68, 115.57, 125.24, 127.49, 128.05, 128.16, 129.08, 131.27, 136.85, 137.70, 142.57, 143.91, 151.635.

1-Benzyl-3-(p-hydroxycarbonylphenyl)selenolo[3,2-c]pyrazole (70)

Compound 67 (0.792 g, 0.002 mole) was used to replace compound 55 in the preparation of compound 59 to afford compound 70. Yield: 0.649 g (85.2%); white crystals; mp 288-290° C.

Compound 70
(1) MS (m/z): 382.0 (M$^+$)
(2) IR, $\nu_{max}$ (KBr) cm$^{-1}$: 1684 (C=O); 2400-3200 (OH)
(3) UV: λmax (MeOH) nm (log ε): 302 (3.8)
(4) $^1$H-NMR (CDCl$_3$, 200 MHz) δ (ppm):
5.60 (s, 2H), 7.20-7.38 (m, 5H), 7.55 (d, 1H, J=5.8 Hz), 7.82 (d, 2H, J=8.2 Hz), 8.01 (d, 2H, J=8.2 Hz), 8.20 (d, 1H, J=5.8 Hz)
(5) $^{13}$C-NMR (CDCl$_3$, 50 MHz) δ (ppm):
54.66, 113.65, 116.42, 125.36, 128.08, 128.26, 129.13, 130.21, 130.64, 136.72, 137.38, 143.01, 151.91, 167.53.

The following Scheme 4 shows the reactants and reaction routes to synthesize the intermediate compounds and the compounds 78-81 of the present invention.

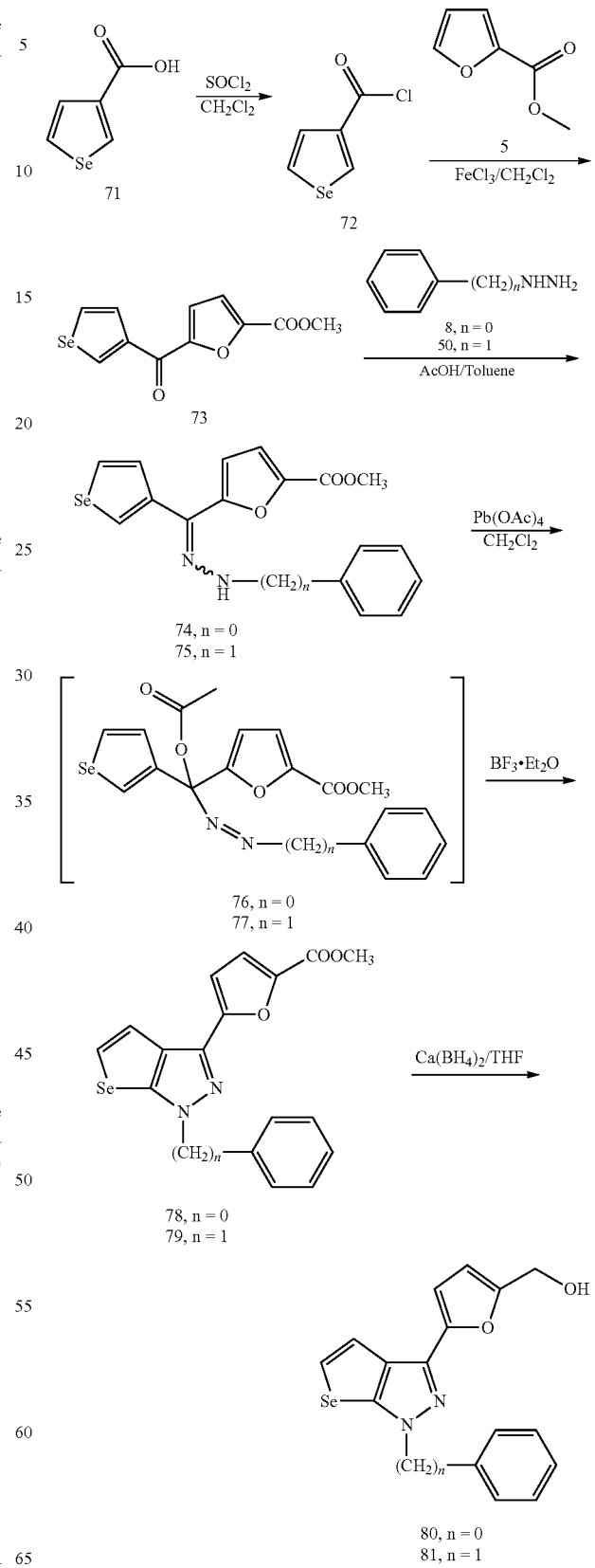

Scheme 4

5-Methoxycarbonyl-2-furyl-3-selenophenyl ketone (73)

To selenophene-3-carboxylic acid 71 (5 g, 0.026 mole) in a three-neck flask 50 ml of dichloromethane and 10 g of $SOCl_2$ were added, and the mixture was reacted under refluxing for 20 h. An intermediate compound 3, selenophene-3-carbonyl chloride, was obtained by evaporating $SOCl_2$ under a reduced pressure. Into the intermediate product 3 was added $CH_2Cl_2$ (50 mL), then methyl furan-2-carboxylate (5.4 g) and anhydrous ferric chloride (4.6 g) were added. The reaction mixture was then heated under refluxing for 4 h, cooled and quenched with water to stop the reaction. The progress of the reaction was monitored by TLC with dichloromethane:n-hexane=4:1. The $CH_2Cl_2$ layer was dried over $MgSO_4$ and filtered. The solvent of the filtrate was evaporated under a reduced pressure, and the residue was subjected to a column chromatography (silica gel) with dichloromethane:n-hexane=4:1, and then recrystallized from dichloromethane to afford compound 73 in white needle crystals (3.0 g). Yield: 40.6%; mp 85-86° C.

Compound 73:
(1) MS (m/z): 284 ($M^+$)
(2) IR, $v_{max}$ (KBr) $cm^{-1}$: 1720 (C=O), 1629 (C=O)
(3) $^1$H-NMR ($CDCl_3$, 200 MHz) δ (ppm):
3.94 (s, 3H), 7.24 (d, 1H, J=3.8 Hz), 7.34 (d, 1H, J=3.8 Hz), 7.92-8.10 (m, 2H), 9.42 (t, 1H, J=1.8 Hz).
(4) $^{13}$C-NMR ($CDCl_3$, 50 MHz) δ (ppm):
52.44, 118.63, 118.92, 130.51, 130.80, 142.12, 142.58, 146.27, 154.59, 158.64, 175.30.

3-(5-Methoxycarbonyl-2-furyl)-1-phenylselenolo[2,3-c]-pyrazole (78)

Compound 73 (3.8 g, 0.013 mole), phenylhydrazine 8 (5.0 g, 0.046 mole) and glacial acetic acid (1.5 ml) were allowed to react as in the preparation of compound 55 to afford compound 78. Yield: 0.62 g (12.8%); white needle crystals; mp 167-169° C.

Compound 78:
(1) MS (m/z): 372.0 ($M^+$)
(2) IR, $v_{max}$ (KBr) $cm^{-1}$: 1725 (C=O)
(3) $^1$H-NMR (DMSO-$d_6$, 200 MHz) δ (ppm):
3.83 (s, 3H), 7.22 (d, 1H, J=3.6 Hz), 7.36 (t, 1H, J=7.0 Hz), 7.45 (d, 1H, J=3.8 Hz), 7.50-7.72 (m, 3H), 7.77 (d, 2H, J=8.2 Hz), 7.93 (d, 1H, J=5.8 Hz).
(4) $^{13}$C-NMR (DMSO-$d_6$, 50 MHz) δ (ppm):
52.42, 110.48, 118.30, 120.67, 127.03, 130.54, 131.37, 136.34, 139.54, 141.80, 143.79, 151.12, 158.71.

1-Benzyl-3-(5-methoxycarbonyl-2-furyl)selenolo[2,3-c]pyrazole (79)

Compound 73 (5.6 g, 0.02 mole), benzylhydrazine 50 (4.88 g, 0.04 mole) and glacial acetic acid (1.5 ml) were allowed to react as in the preparation of compound 55 to afford compound 79. Yield: 0.82 g (10.6%); white crystals;
mp 121-123° C.

Compound 79:
(1) MS (m/z): 385.8 ($M^+$)
(2) IR, $v_{max}$ (KBr): 1724 (C=O)
(3) $^1$H-NMR ($CDCl_3$, 600 MHz) δ (ppm):
3.89 (s, 3H), 5.42 (s, 2H), 6.85 (d, 1H, J=3.6 Hz), 7.11-7.65 (m, 8H).

3-(5-Hydroxymethyl-2-furyl)-1-phenylselenolo[2,3-c]pyrazole (80)

1.98 g (0.018 mole) of granular anhydrous calcium chloride, 1.377 g (0.036 mole) of sodium brorhydride and 100 ml of anhydrous THF were reacted at room temperature for 4 h to form a white dispersion of calcium borohydride ($Ca(BH_4)_2$). To the dispersion compound 78 (0.744 g, 0.002 mole) was added and was reduced by heating under refluxing for 24 h. The progress of the reduction reaction was monitored by TLC with ethyl acetate (EA):n-hexane=3:2. When the reaction was completed, the reaction mixture was cooled to room temperature, and THF was evaporated under a reduced pressure. The remaining reaction mixture was poured into water to stop the reaction, and then was extracted with chloroform. The organic layer was recovered, dried over $MgSO_4$ and filtered. The solvent of the filtrate was evaporated under a reduced pressure, and the residue was subjected to a column chromatography with EA:n-hexane=3:2, and then recrystallized from EA to afford compound 80 in white crystals (0.612 g). Yield: 88.9%;
mp 136-138° C.

Compound 80:
(1) MS (m/z): 344.1 ($M^+$)
(2) IR, $v_{max}$ (KBr) $cm^{-1}$: 3200-3600 (OH)
(3) $^1$H-NMR (DMSO-$d_6$, 200 MHz) δ (ppm):
4.48 (d, 2H, J=5.6 Hz), 5.35 (t, 1H, J=5.8 Hz), 6.46 (d, 1H, J=3.0 Hz), 6.98 (d, 1H, J=3.0 Hz), 7.31 (t, 1H, J=7.6 Hz), 7.50-7.70 (m, 3H), 7.75 (d, 2H, J=8.0 Hz), 7.85 (d, 1H, J=5.6 Hz).
(4) $^{13}$C-NMR (DMSO-$d_6$, 50 MHz) δ (ppm):
56.20, 109.49, 117.86, 118.84, 126.43, 130.03, 130.45, 130.72, 137.79, 139.69, 141.18, 146.77, 156.51.

1-Benzyl-3-(5-Hydroxymethyl-2-furyl)selenolo[2,3-c]pyrazole (81)

1.98 g (0.018 mole) of anhydrous calcium chloride, 1.377 g (0.036 mole) of sodium brorhydride and 50 ml of anhydrous THF were reacted at room temperature for 4 h to form calcium borohydride ($Ca(BH_4)_2$). To the reaction mixture compound 79 (0.772 g, 0.002 mole) was added and was reduced by heating under refluxing for 6 h. The reaction mixture was poured into icewater to stop the reaction, and then was extracted with dichloromethane. The organic layer was recovered, dried over $MgSO_4$ and filtered. The solvent of the filtrate was evaporated under a reduced pressure, and the residue was subjected to a column chromatography with EA:n-hexane=1:2, and then recrystallized from n-hexane to afford compound 81 in white crystals (0.457 g).
Yield: 63.8%; mp 130.2-131.3° C.

Compound 81:
(1) MS (m/z): 358 ($M^+$)
(2) IR, $v_{max}$ (KBr) $cm^{-1}$: 3100-3400 (OH)
(3) $^1$H-NMR (DMSO-$d_6$, 200 MHz) δ (ppm):
4.42 (d, 2H, J=5.6 Hz), 5.31 (t, 1H, J=5.6 Hz), 5.43 (s, 2H), 6.38 (d, 1H, J=3.2 Hz), 6.76 (d, 1H, J=3.2 Hz), 7.20-7.50 (m, 6H), 7.57 (d, 1H, J=5.8 Hz).
(4) $^{13}$C-NMR (DMSO-$d_6$, 50 MHz) δ (ppm):
56.01, 56.15, 107.73, 109.31, 118.73, 128.73, 129.03, 129.22, 135.74, 135.86, 143.39, 147.59, 155.60.

Cell Culture and Treatment

The human lung cancer cell lines (NCI-H226) and human renal cancer cell lines (A-498) were purchased from the ATCC (Manassas, Va.). The NCI-H226 and A498 cells were cultured in RPMI-1640 and DMEM medium (GIBCO) respectively, supplemented with 10% FBS, penicillin (100 unit/mL)/streptomycin (100 μg/mL) and 1% L-glutamine. All cells were grown in a humidified atmosphere containing 5% $CO_2$ at 37° C.

Cytotoxicity Assay

The cytotoxicity was assessed using 3-(4,5-dimethylthiazol-2-yl)-2,5-diphenyltetrazolium bromide (MTT) assay. NCI-H226 and A498 cells were seeded at $1\times10^4$ cells/well into 96-well plates. After 24 h incubation to allow for cell attachment, cells were treated with test compounds for 48 h. After treatment, cells were washed once with PBS and incubated with 1 mg/ml MTT (Sigma, St. Louis, Mo., USA) for 2 h. Then the formazan precipitate was dissolved in 150 mL DMSO and the absorbance was measured on an ELISA reader at a best wavelength of 570 nm.

TABLE 1

Cytotoxicity of selenolo[3,2-c]pyrazole and selenolo[2,3-c]pyrazole derivatives against NCI-H226 and A498 cancer cell lines

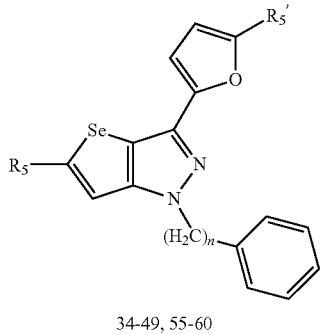

34-49, 55-60

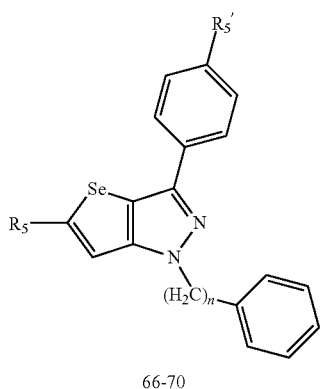

66-70

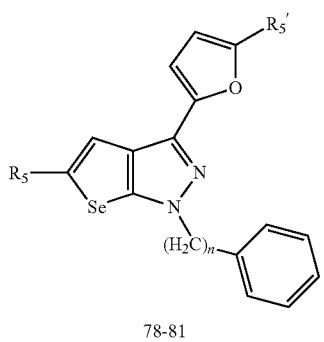

78-81

| Compound | $R_5$ | n | $R_{5'}$ | IC$_{50}$ (μM) NCI-H226 | A498 |
|---|---|---|---|---|---|
| 34 | H | 0 | COOCH$_3$ | >100 | >100 |
| 35 | CH$_3$ | 0 | COOCH$_3$ | >100 | >100 |
| 36 | H | 0 | COOCH$_3$ | >100 | >100 |
| 37 | H | 0 | COOCH$_3$ | >100 | >100 |
| 38 | H | 0 | COOCH$_3$ | >100 | >100 |

TABLE 1-continued

Cytotoxicity of selenolo[3,2-c]pyrazole and selenolo[2,3-c]pyrazole derivatives against NCI-H226 and A498 cancer cell lines

| 39 | H | 0 | COOCH$_3$ | >100 | >100 |
|---|---|---|---|---|---|
| 40 | H | 0 | COOCH$_3$ | >100 | >100 |
| 41 | H | 0 | COOCH$_3$ | >100 | >100 |
| 42 | H | 0 | COOCH$_3$ | >100 | >100 |
| 43 | H | 0 | CH$_2$OH | 29.5 | 2.2 |
| 44 | CH$_3$ | 0 | CH$_2$OH | 25.0 | 1.98 |
| 48 | H | 0 | COOH | >100 | >100 |
| 49 | CH$_3$ | 0 | COOH | >100 | >100 |
| 55 | H | 1 | COOCH$_3$ | >100 | >100 |
| 56 | CH$_3$ | 1 | COOCH$_3$ | >100 | >100 |
| 57 | H | 1 | CH$_2$OH | 1.4 | 0.4 |
| 58 | CH$_3$ | 1 | CH$_2$OH | 8.7 | 0.9 |
| 59 | H | 1 | COOH | >100 | >100 |
| 60 | H | 1 | CH$_2$OCO(CH$_2$)$_2$COOH | 2.2 | 0.8 |
| 66 | H | 0 | COOCH$_3$ | >100 | >100 |
| 67 | H | 1 | COOCH$_3$ | >100 | >100 |
| 68 | H | 0 | CH$_2$OH | >100 | >100 |
| 69 | H | 1 | CH$_2$OH | >100 | >100 |
| 70 | H | 1 | COOH | >100 | >100 |
| 78 | H | 0 | COOCH$_3$ | >100 | >100 |
| 79 | H | 1 | COOCH$_3$ | >100 | >100 |
| 81 | H | 1 | CH$_2$OH | — | 0.14 |

[a]Data was presented as IC$_{50}$ (μM, the concentration of 50% proliferation-inhibitory effect). Values are expression as the mean ± S.D. of three independent experiments. Student's t tests were used to assess the statistical significance of the differences, with "P" values of less than 0.05 being considered statistically significant.

It can be seen from Table 1 that compound 43, 44, 57, 58, 60 and 81 have significant potency in inhibiting proliferation of NCI-H226 and A498 human cancer cell lines.

The invention claimed is:

1. A selenolopyrazole compound having a formula (I) or (II):

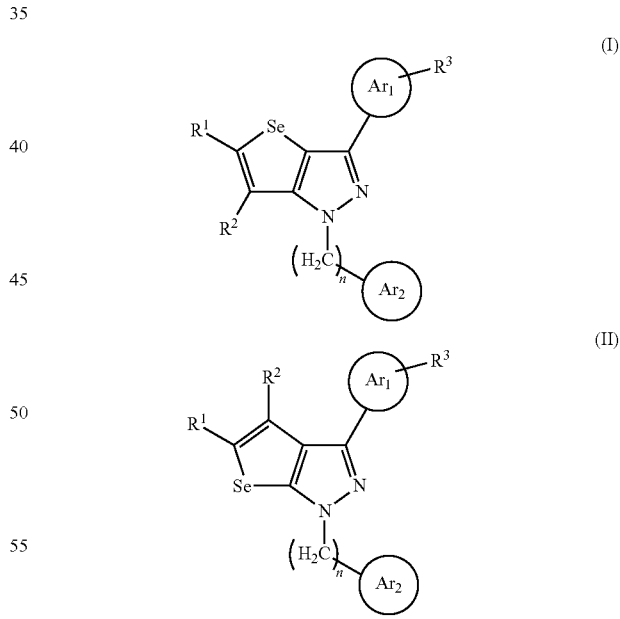

wherein $R^1$ is hydrogen, C1-C6 alkyl, hydroxyl, C1-C6 alkoxyl, F, Cl, or Br;

$R^2$ is hydrogen or methyl;

$R^3$ is —COOR$^2$, —(CR$^2$H)$_j$OH, —(CR$^2$H)$_j$—C(O)—(CH$_2$)$_m$—COOH, —(CR$^2$H)$_j$—O—C(O)—(CH$_2$)$_m$—NH$_2$ or —(CR$^2$H)$_j$—O—C(O)—(CH$_2$)$_m$—COOH, wherein $R^2$ is defined as above, j=1-6 and m=1-6;

Ar₁ is phenyl or

wherein x is O, S or Se;
Ar₂ is

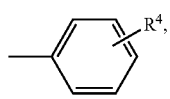

wherein $R^4$ is hydrogen, C1-C6 alkyl, hydroxyl, C1-C6 alkoxyl, F, Cl, or Br; and n=0, 1 or 2.

2. The compound as claimed in claim 1, wherein Ar₁ is 2-furyl.

3. The compound as claimed in claim 2, wherein $R^3$ is 5-CH₂OH or 5-CH₂—O—C(O)—(CH₂)$_m$—COOH, wherein m=1 or 2.

4. The compound as claimed in claim 2, wherein $R^3$ is 5-CH₂OH.

5. The compound as claimed in claim 2, wherein $R^3$ is 5-CH₂—O—C(O)—(CH₂)₂—COOH.

6. The compound as claimed in claim 3, wherein n=0 or 1.

7. The compound as claimed in claim 6, wherein $R^2$ and $R^4$ are both hydrogen, and $R^1$ is hydrogen or methyl.

8. The compound as claimed in claim 2, wherein the compound has the formula (I).

9. The compound as claimed in claim 2, wherein the compound has the formula (II).

10. An anticancer pharmaceutical composition, wherein the cancer is human lung cancer or human renal cancer comprising a therapeutically effective amount of the compound (I) or (II) as set forth in claim 1, or a pharmaceutically acceptable salt thereof.

11. A method of inhibiting growth of cancer cells, wherein the cancer is human lung cancer or human renal cancer comprising administering the compound (I) or (II) as set forth in claim 1, or a pharmaceutically acceptable salt thereof, to a subject suffering said cancer in need of said inhibition.

12. The method as claimed in claim 11, wherein Ar₁ is 2-furyl.

13. The compound as claimed in claim 12, wherein $R^3$ is 5-CH₂OH or 5-CH₂—O—C(O)—(CH₂)$_m$—COOH, wherein m=1 or 2.

14. The method as claimed in claim 12, wherein $R^3$ is 5-CH₂OH.

15. The method as claimed in claim 12, wherein $R^3$ is 5-CH₂—O—C(O)—(CH₂)₂—COOH.

16. The method as claimed in claim 13, wherein n=0 or 1.

17. The method as claimed in claim 16, wherein $R^2$ and $R^4$ are both hydrogen, and $R^1$ is hydrogen or methyl.

18. The method as claimed in claim 12, wherein the compound has the formula (I).

19. The method as claimed in claim 12, wherein the compound has the formula (II).

* * * * *